United States Patent [19]

Siren

[11] Patent Number: 5,051,411
[45] Date of Patent: Sep. 24, 1991

[54] A METHOD OF ACHIEVING AN IMMUNOSUPPRESSIVE EFFECT

[75] Inventor: Matti Siren, Montagnola/Lugano, Switzerland

[73] Assignee: Perstorp AB, Perstorp, Sweden

[21] Appl. No.: 367,968

[22] Filed: Jun. 19, 1989

Related U.S. Application Data

[63] Continuation-in-part of Ser. No. 251,566, Sep. 30, 1988, Pat. No. 5,023,248, and a continuation-in-part of Ser. No. 173,985, Mar. 28, 1988, Pat. No. 5,019,566, which is a continuation-in-part of Ser. No. 38,230, Apr. 14, 1987, abandoned, which is a continuation-in-part of Ser. No. 15,679, Feb. 17, 1987, Pat. No. 4,797,390, which is a continuation-in-part of Ser. No. 788,801, Oct. 18, 1985, Pat. No. 4,735,936.

[30] Foreign Application Priority Data

Oct. 23, 1984 [SE] Sweden .............................. 8405295-0
Apr. 16, 1986 [SE] Sweden .............................. 8601709-2

[51] Int. Cl.$^5$ ............................................ A01N 57/00
[52] U.S. Cl. ..................................................... 514/103
[58] Field of Search ......................................... 514/103

[56] References Cited

U.S. PATENT DOCUMENTS 2,723,938 11/1955 Buckwalter et al. ................ 514/103
3,591,665 7/1971 Kimura et al. ............. 252/400.2 XR

OTHER PUBLICATIONS

Lim et al., Biochim. Biophys. Acta 302, 316–328 (1973).
Tomlinson et al., Biochemistry, 1, No. 1, 166–171 (1962).
Kerr et al., Arch of Biochem & Biophys, 96, 347–352 (1962).
Suematsu et al., Biochem. & Biophys. Res. Comm., 120, No. 2, 481–485 (1984).
Desjobert, Bull. Ste. Chim. Biol., 36, No. 9, 1293–1299 (1954).
Streb et al., Nature, 306, 67–68 (1983).
Irvine et al., Biochem J., 223, 237–243 (1984).

*Primary Examiner*—Stanley J. Friedman
*Assistant Examiner*—T. Criares
*Attorney, Agent, or Firm*—Scully, Scott, Murphy & Presser

[57] ABSTRACT

A method of reducing the negative effects of heavy metals and a method of preventing or alleviating immunodeficiency, hypertension and dermatitis in mammals is disclosed. In these methods pharmaceutical compositions are administered to a mammal in need thereof. The particular pharmaceutical composition includes a reducing, preventing or alleviating effective amount, for the particular condition, of at least one isomer of inositol triphosphate.

2 Claims, No Drawings

A METHOD OF ACHIEVING AN IMMUNOSUPPRESSIVE EFFECT

REFERENCE TO RELATED APPLICATIONS

This is a continuation-in-part of U.S. patent application, Ser. No. 251,566, filed Sept. 30, 1988 now U.S. Pat. No. 5,023,248, is a continuation-in-part of U.S. patent application, Ser. No. 173,985, filed Mar. 28, 1988 now U.S. Pat. No. 5,019,566, which is a continuation-in-part of U.S. patent application, Ser. No. 38,230, filed Apr. 14, 1987 (abandoned), which is a continuation-in-part of U.S. patent application, Ser. No. 15,679, filed Feb. 17, 1987, now U.S. Pat. No. 4,797,390, which is a continuation-in-part of U.S. patent application, Ser. No. 788,801, filed Oct. 18, 1985, now U.S. Pat. No. 4,735,936.

FIELD OF THE INVENTION

The present invention relates to the treatment and alleviation of conditions caused or aggravated by the presence of lead, mercury, nickel or chromium in the body, a method of preventing or alleviating different conditions in the body by administering thereto a pharmaceutical composition containing at least one specific isomer of inositol triphosphate ($IP_3$) for such treatment.

BACKGROUND OF THE INVENTION

Even as early as the year 1900, different researchers had reported the finding of the organic phosphate compound phytic acid, i.e. 1.2.3.4.5.6-hexakis (dihydrogenphosphate) myo-inositol (also sometime called inositolhexaphosphoric acid) in plants. The content in grain is usually approximately 0.5–2%, with certain exceptions. Polished rice has a level of only 0.1% while wild rice contains as much as 2.2% phytic acid. Beans contain about 0.4–2%, oil plants approximately 2–5% and pollen 0.3–2%. The content of phytic acid in the plant varies during the growth period. The content is also influenced by, among other things, the climate.

In the literature there are reports on the presence of inositol pentaphosphate ($IP_5$) and inositol tetraphosphate ($IP_4$) in a few plants. It is further known that phosphate derivatives lower than $IP_6$ are formed at germination of grain. For instance the final products at the germination are inositol and phosphate. The use of $IP_6$ has been described in several scientific publications. The majority of the authors of these articles have observed several negative effects on humans and animals when consuming $IP_6$ or substances containing $IP_6$. Feeding dogs with too high an amount of $IP_6$ gives rise for example to rachitis. In humans lack of zinc and as a consequence thereof slower growth of children has been observed. Anemia has been observed mainly in women. Because of the above mentioned negative effects on the mineral balance in humans and animals, attempts have so far been made to reduce the intake of $IP_6$ and its derivatives to a minimum.

From C. A. Vol. 33 (1939), Abstr. No. 7351, No. 3/4 the use of phosphates including inositol phosphates as an anti-rachitic diet has been reported. No reference is made to specific inositol phosphates and nothing has been said in regard to complexing of metals.

U.S. Pat. No. 4,473,563 discloses the extra corporal treatment of erythrocytes to incorporate therein inositol phosphates to improve the oxygen supply. Then erythrocytes are separated from drawn blood which has been pumped out of the body for that purpose. After complicated treatment of erythrocytes the latter are re-introduced into the blood. There is no disclosure of administering inositol phosphates directly to the body. Moreover, nothing has been said in regard to treatment and alleviation of conditions caused or aggravated by the presence of lead, mercury, nickel or chromium in the body by a specially selected inositol phosphate.

In U.S. Pat. No. 2,723,938 the use of inositol phosphates is disclosed for stabilizing dispersions of acqueous suspension of penicillin. This ensures that brief simple manual shaking will restore a state of complete and uniform dispersion of the penicillin after prolonged storage.

For several hundred years metals in different forms have been used for instance at industrial processes. Early it was understood that certain metals, especially arsenic, lead and mercury are poisonous for humans.

The research relating to the physiological influence of metals on humans for instance has gone on all the time. It has got an increased importance during the last few decades, since people to an increasing extent are exposed to poisonous metals due to industrial discharges and other changes of the environment.

Many metals are necessary for the body. However, in too high concentrations these metals can give harmful effects. This case is valid for instance for iron, copper, zinc and magnesium. Thus, there is an indistinct limit between harmful and harmless/essential metals.

Non-essential metals can cause biological damages by interfering in biochemical processes. The metals or their ions can bind to biologically important molecules, negatively co-operate with enzymes and nucleic acids and influence the properties of cell membranes so that the normal function is disturbed.

To this group of metals firstly lead, mercury, nickel and chromium belong; and secondly arsenic, thallium, plutonium, barium, tin, copper and cobolt. In solution the metals are mainly present in the form of ions.

For natural reasons an acute supply of metals at a high concentration causes a temporarily increased resorption with acute damages on biological processes. A long exposure to metals results in a accumulation in the organism, among other things in the tissues and a rather slow secretion of the metals. Thus, the effects of acute respectively chronical metal poisoning become different. Synergistical damaging effects can occur when the organism is exposed to several metals.

Lead poisoning is a very serious problem due to the rather usual presence of lead in the environment. Acute effects of lead poisoning can result in inflammatory damages, damages on the intestine, cardiovascular damages and shock conditions. The metals can also give rise to disorders in hormon glands, such as hypophysis, adrenal gland and thyroid gland. This fact is mostly evident for mercury. Chronical effects of lead poisoning can cause cardiovascular damages and hypertension but also brain damages and neurological disorders.

Poisoning caused by mercury can acutely give rise to kidney damages, liver damages, lung damages and damages on the intestine. Chronical effects are for instance mental damages, nerve disorders and effects on the immunity defence, which cause for example autoimmune diseases.

Nickel is resorbed to a rather great proportion in the intestine. Acute damages due to nickel poisoning can occur in the form of neurological disorders, while chronical damages can result in allergies and certain kinds of cancer.

Acute damages caused by chromium poisoning can arise in the intestine, while certain kinds of allergies can be found at chronical exposure of the metal.

Moreover, it is previously known that the metals influence many enzyme systems, especially those containing thiol groups. Furthermore, the metals influence the metabolism in the second messenger system. Nickel and lead have in vitro caused a decrease of the DNA-synthesis.

The influence of nickel on zinc depending enzymes such as carbonylanhydrase results in an absence of enzyme activity.

Lead inhibits the enzyme xantinoxidase, while lead as well as mercury inhibit guanine aminohydrolase.

Metal chelates of different kinds, for example BAL (2.3-dimercapto propanol) and EDTA (ethylenediamino tetraacetic acid) have been used to cure or alleviate conditions caused by metal poisonings.

The chelates used so far have, however, negative properties, which has resulted in an insignificant clinical use. Thus, BAL is not soluble in water. Furthermore, it gives rise to a bad smell at the use. Its non-specific chelating ability also results in negative effects on the mineral balance concerning essential metals.

EDTA is resorbed to a low extent which is a limitation, since oral administration cannot be used.

Since the secretion velocity of this substance is high, rather high doses must be added to get an effect. However, this result in a disorder of the calcium level in the organism.

SUMMARY OF THE INVENTION

According to the present invention it has quite unexpectedly been found possible to solve the above mentioned negative effects of toxic metals such as lead, mercury, nickel or chromium on humans and animals and thus also to prevent or alleviate the connected diseases. Thus, a method of reducing the negative effects of the above mentioned metals in body tissues has been brought about. At said method a pharmaceutical composition comprising an amount of at least one specific isomer of inositol triphosphate sufficient to interfere with toxic metals such as lead, mercury, nickel or chromium is administered to a human or an animal.

In addition, the present invention relates to a method of preventing or alleviating some conditions which may or may not be connected to the above mentioned metals by administering to a human or an animal a pharmaceutical composition comprising an amount of at least one specific isomer of inositol triphosphate sufficient to obtain said prevention or alleviation.

DETAILED DESCRIPTION OF PREFERRED EMBODIMENTS

As examples of the diseases which the composition according to the invention is useful to prevent or alleviate, metal intoxication, allergy caused by any one of these metals, inflammatory conditions, damage to the connective tissue, liver damage, brain damage, immunodeficiency or to restore or normalize the immune response, conditions of shock, gastroenteritis, dermatitis and neurological disturbances can be mentioned.

In addition, the following diseases can be mentioned; cell proliferative changes, cancer, cardiovascular diseases, high blood pressure, damage to the central nervous system, damage to the lungs and kidney damage.

It is believed that at least some of the above diseases are caused or aggravated by the presence of toxic metals such as lead, mercury, nickel or chromium, but the invention is not limited by said theory, since the method according to the invention is useful against said diseases whatever reason for them.

For production of the isomer or isomers of $IP_3$ which accomplish the above objectives and which is present in the composition according to the invention, one or more of the compounds $IP_6$, $IP_5$ or $IP_4$ or a natural product containing at least one of these compounds can be used as a starting material. In the cases where the starting material is a natural product, one with a content of at least 0.3%, preferably at least 1% of inositol phosphate ($IP_6 + IP_5 + IP_4$) is preferably chosen. Particularly suitable products are beans, bran, pollen and oil plants.

The composition according to the present invention should preferably contain at least 10%, preferably at least 20%, or better yet at least 40% $IP_3$ calculated on the inositol content of the starting material. As high a level as possible of $IP_3$ in the composition is aimed at, as $IP_3$ has the best therapeutic effect according to experiments shown below. The $IP_3$ isomers present in the composition according to the invention can, for example, be produced by:

1) Enzymatic breakdown starting from $IP_4$, $IP_5$ and/or $IP_6$.
2) Chemical hydrolysis starting from $IP_4$, $IP_5$ and/or $IP_6$.
3) Chemical synthesis starting, for example, with inositol, $IP_1$, $IP_2$ and phosphate.
4) Enzymatic synthesis starting for example with from inositol, $IP_1$, $IP_2$ and phosphate.
5) Microbiological production (including also hybrid DNA-techniques).
6) Chemical or enzymatic migration of inositol phosphate or
7) Chemical or enzymatic hydrolysis of substituted inositol phosphate.

A combination of two or more of the above mentioned procedures may also be used.

According to the invention a procedure where the above mentioned higher inositol phosphates $IP_6$, $IP_5$ and/or $IP_4$ are broken down enzymatically to $IP_3$ with phytase enzyme, for instance, is preferred. Phytase enzyme is normally present in all inositol phosphate containing plants and seeds. Because of this it is, according to the invention, usually not necessary to add the enzyme if a natural product is used as starting material. In the cases where the natural product has too low an enzymatic activity or when $IP_6$, $IP_5$ or $IP_4$ or a mixture of these is used as starting material, a phytase enzyme, for example, from bran is added.

A suitable way to treat the natural or crude starting material is to pretreat it, for instance by breakage or removal of outer membrane and removal of unwanted constituents. Thus, when using pollen the allergens should be removed. Thereafter, the material is soaked in water to make the inositol phosphate available for breaking down and to activate the enzyme. In the cases where an extra quantity of enzymes is necessary, this quantity is added at this stage. The enzyme is then allowed to act for so long a time as is necessary for the intended degree of hydrolysis to be achieved.

The hydrolysis takes place at a suitable temperature, usually 20°–70° C., preferably 30°–40° C. and at optimal pH-level for the phytase present. In order to stop the hydrolysis at the intended level the enzyme may be destroyed or inactivated, for instance by a rapid heating of the hydrolysed starting material. This also ensures that an uncontrolled and undesired continued hydrolysis of $IP_3$ in the stomach will not continue when the composition is administered. In order to transfer the material to a form which is stable at storage it can suitably be freeze dried.

Yeast can be used advantageously as a source of phytase. Preferably baker's yeast is used. When using yeast essentially only one isomer of $IP_3$ is obtained, namely D-myo-inositol-1.2.6-triphosphate.

The above mentioned procedure, in applicable parts with possible modifications, can be used also when one or more of the compounds $IP_6$, $IP_5$ or $IP_4$ per se are used as starting material.

The pharmaceutical composition used in the method according to the invention comprises as a pharmaceutically active ingredient at least one isomer of inositol triphosphate ($IP_3$) in an amount sufficient to reduce the negative effect of lead, mercury, nickel or chromium in the body.

It is suitable that the composition according to the invention exists in unit dosage form. Tablets, granulates or capsules are suitable administration forms for such unit dosage. Furthermore, tablets and granulates can easily be surface treated such as to provide an enteric coating to prevent an uncontrolled hydrolysis in the stomach and to bring about a desired absorption in the intestine. Other suitable administrtion forms are slow release and transdermal administration. A usual pharmaceutically acceptable additive, excipient and/or carrier can be included in the composition. The tablets or granulates can also contain a disintegrant which causes the tablets or the granulates respectively to disintegrate easily in the intestine. In certain cases, especially in acute situations, it is preferable to use the unit dosage in the form of a solution for intravenous administration.

The pharmaceutical composition can also consist as such of $IP_3$ solely without any additive, excipient or carrier.

If desired, the composition can be free of other inositol phosphates, $IP_1$, $IP_2$, $IP_4$, $IP_5$ and $IP_6$. Accordingly, the mixture of $IP_3$ isomers can have a purity of 90–100%, such as 93–100% or preferably 95–100%.

Alternativley, the pharmaceutical composition used in the method can consist of or comprise one or more specific $IP_3$ isomers disclosed hereinafter, each present in substantially pure form. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

The production of $IP_3$ and the isolation of the different isomers thereof are disclosed in the U.S. Pat. No. 4,777,134.

It is in most cases suitable that the $IP_3$-isomer or isomers in the composition used according to the invention is present in salt form in order not to affect the mineral balance negatively. The salt should preferably consist of a sodium, calcium, zinc or magnesium salt or a mixture of two or more of these salts. Calcium and zinc salts or mixtures of these are especially preferred. The isomer of $IP_3$ can also partly be present as a salt of one or more physiologically acceptable compounds in the lanthanide series.

For the above mentioned reasons it is also an advantage if the composition contains a surplus or an extra addition of at least one pharmaceutically acceptable salt of calcium, zinc or magnesium with a mineral acid or organic acid. This is especially valuable for older persons who are often deficient in these minerals.

The composition used according to the present invention can preferably also contain at least one substance containing selenium, an unsaturated fatty acid, such as gamma linoleic acid, vitamin E, vitamin C or a pharmaceutically acceptable organic acid or salt thereof, such as citrate, oxalate, malonate and tartrate. These substances also help to counteract the negative effect of lead, mercury, nickel and/or chromium in the body and/or to give in addition thereto, in certain cases, a desirable effect together with the $IP_3$ isomer in the composition. The content of selenium in the composition is preferably such that the daily intake is about 0.7–8 ug/kg body weight, preferably 0.7–3.3 ug. For vitamin E the corresponding values are about 0.1–2 mg and 0.1–1 mg respectively.

The composition is suitably free from penicillin.

For administration to human patients appropriate dosages can routinely be determined by those skilled in this art by extention of the results obtained in animals at various dosages. The preferred dosage for humans falls within the range of 0.1 to 100 mg, especially 0.1–50 mh $IP_3$/day/kg body weight.

In animal experiments, no toxic effects were seen after administration of very high doses of $IP_3$, 160 mg/kg body weight by intravenous injection to mice or 1600 mg/kg body weight by intraperitoneal injection to mice.

The composition used according to the present invention preferably contains at lease one, sometimes two or more of the following substances, which correspond to an essential $IP_3$-isomer or isomers having the structural formula

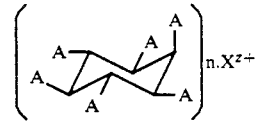

where three of the A's are OH and three of the A's are $OPO_3{}^{2-}$, X is hydrogen and/or at least one univalent, divalent or multivalent cation; n is the number of ions; and z is the charge of the respective ions.

In a preferred embodiment n is an integer between 6 and 1 inclusive, z is an integer ranging between 1 and 6 inclusive, n is an integer preferably between 3 and 6 and z is an integer of 1, 2 or 3.

Among the $IP_3$-isomers within the contemplation of the above structural formula, the following $IP_3$ compounds are preferred:

D-myo-inositol-1.2.6-triphosphate of the formula

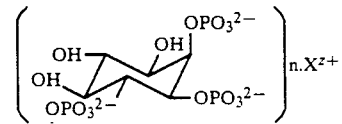

where X is hydrogen, at least one univalent, divalent or multivalent cation, or a mixture thereof, n is the number of ions, and z is the charge of the respectively ion;

D-myo-inositol-1.2.5-triphosphate of the formula

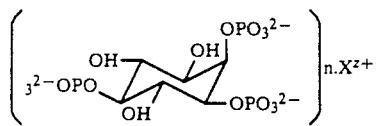

where X, n and z have the above mentioned meaning;

myo-inositol-1.2.3.-triphosphate of the formula

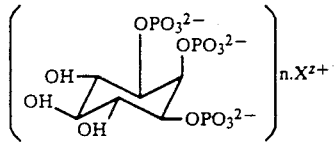

where X, n and z have the above mentioned meaning;

L-myo-inositol-1.3.4-triphosphate of the formula

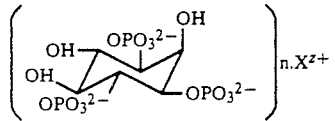

where x, n and z have the above mentioned meaning.

In each of the above formulas n rangesbetween 6 to 1 inclusive and z ranges from1 to 6 inclusive. Preferably, n is between 3 to 6 inclusive and z is 3, 2 or 1. Of above isomers D-myo-inositol-1,2,6-triphosphate is preferred.

Other inositol triphosphate isomers that may be utilized in the present invention as the active $IP_3$ ingredient in the composition has the structural formula

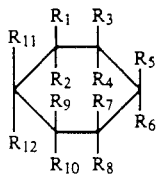

One group of inositol triphosphate compounds are defined by structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol triphosphates are defined by structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol triphosphates are defined by structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol triphosphates are defined by structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol triphosphates are defined by structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol triphosphates are defined by structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet group of inositol triphosphates are defined by structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol triphosphates are defined by structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol triphosphate compounds within the contemplation of the above groups include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ an $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$, $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above discussed compounds having structural formula (I) are made by the procedure set forth in Examples 14 to 17.

IP$_3$ may be the sole pharmaceutically active ingredient in the composition used. However, also other pharmaceutically active ingredients can be present therein. The amount of IP$_3$ should then constitute 5 to 95 or 15 to 80, such as 25 to 60 per cent by weight of said active ingredients.

Moreover, the composition can be a multi-vitamin unit containing 2 to 60, such as 2 to 40 or preferably 2 to 25 percent by weight of IP$_3$ based on the total weight of pharmaceutically active ingredients.

The composition usually contains 0.01–1.5 g, such as 0.05–1.3 or preferably 0.1–1 g of IP$_3$.

In some applications of the method the pharmaceutical composition used comprises a source of IP$_3$.

The invention is further explained below in connection with enclosed FIG. 1 and embodiment examples of which example 1 shows experiments relating to the relative complex constants for lead, chromium, nickel and mercury respectively to IP$_3$. Example 2 illustrates an experiment concerning the complex constant of lead to IP$_3$. Example 3 relates to experiments on structural changes of the cell membranes in the presence of Pb, Ni or Cr and the use of IP$_3$ to counteract such changes.

Example 4 illustrates experiments on the damaging effect of Pb, Hg and Cr on erythrocyte cell membrane. Examples 5–11 show production of IP$_3$ and separation thereof into different isomers. In Example 12 the manufacture of a solution of a potassium salt of D-myo-inositol-1.2.6-triphosphate for injection is shown. Example 13 describes manufacture of tablets of a calcium salt of D-myo-inositol-1.2.6-triphosphate. FIG. 1 shows the result of the experiments according to example 1. Example 14 shows production of D-chiro-inositolhexaphosphate, while Example 15 illustrates production of D-chiro-inositoltriphosphate. In Example 16 the production of epi-inositolhexaphosphate is shown, while the conversion thereof to epi-inositoltriphosphate is illustrated in Example 17. Example 18 shows the positive effect regarding decrease of hypertension by administration of D-myo-inositol-1.2.6-triphosphate (IP$_3$).

Example 19 illustrates normalization of the immune system by administering of IP$_3$. Example 20 relates to treatment of skin inflammation with IP$_3$.

EXAMPLE 1

The relative complex constants for D-myo-inositol-1.2.6-triphosphate (IP$_3$) and lead, chromium, nickel and mercury respectively were determined.

A solution consisting of 4 mM IP$_3$ was titrated with 100 mM NaOH. Similar titrations were performed in the presence of Pb, Ni, Hg (12 mM) or Cr (8 mM).

A strong metal complex will result in a lowering of pH at a certain amount NaOH added. FIG. 1 shows the performed titrations and the relative metal binding properties. At pH 9, the binding properties are as follows: Pb<Ni<Cr<Hg.

As can be seen IP$_3$ binds each of the metals very strongly.

EXAMPLE 2

The binding constant for the complex D-myo-inositol-1.2.6-triphosphate-lead was determined with NMR.

By comparing the signal intensities and ratios in $^{32}$P-NMR as a function of the amount of lead added to an inositoltriphosphate solution the binding constant (K) for the complex was calculated to be $10^8$.

EXAMPLE 3

The structure of the cell membrane is very essential for the proper function of the cell. It is known that the presence of Fe (II) in liposomes (phospholipids from oxbrain) damages the cell membrane. One measurement of the damage is the determination of the lipidperoxides formed when the metal is added to the preparation.

In this example, the synergistic damaging effects of the cell membrane when Pb, Ni and Cr is added to the preparations together with Fe (II), were investigated. Furthermore the preventive effect of the presence of D-myo-inositol-1.2.6-triphosphate (IP$_3$) was evaluated.

| Reaction mixture | |
|---|---|
| Clark-Lubs buffer pH 5.5 | 40 mM |
| Liposomes, Sigma type VII | 1 mg/ml |
| IP$_3$ | 1.0 mM |
| (NH$_4$)$_2$ Fe(SO$_4$)$_2$ | 0.1 mM |
| Pb$^{2+}$, Ni$^{2+}$, Cr$^{3+}$ respectively | 0.4 mM |

The reaction mixture (1.0 ml) was incubated for 2 hours at 37° C. After incubation 0.5 ml of thiobarbituric acid and 0.5 ml 25% HCl were added and the mixture was heated at 100° C. for 20 minutes. The amount of lipid peroxides was measured by measuring the absorbance at 532 nm.

| Experiment | Metal concentration (mM) | | | | | Absorbance |
| | Fe | Pb | Ni | Cr | IP$_3$ | |
|---|---|---|---|---|---|---|
| 1 | — | — | — | — | — | 0.044 |
| 2 | 0.1 | — | — | — | — | 0.47 |
| 3 | 0.1 | — | — | — | 1.0 | 0.25 |
| 4 | 0.1 | 0.4 | — | — | — | 0.54 |
| 5 | 0.1 | 0.4 | — | — | 1.0 | 0.37 |
| 6 | 0.1 | — | 0.4 | — | — | 0.76 |
| 7 | 0.1 | — | 0.4 | — | 1.0 | 0.34 |
| 8 | 0.1 | — | — | 0.4 | — | 0.57 |
| 9 | 0.1 | — | — | 0.4 | 1.0 | 0.26 |

The structural change of the cell membranes caused by Fe (II) (Experiment 2) was strongly increased by the presence of Pb (Experiment 4), Ni (Experiment 6) or Cr (Experiment 8). These effects were counteracted by IP$_3$ (Experiment 5, 7 and 9).

A disfunction of the cell caused by disturbances in the structure of the cell membrane can be linked to many diseases.

EXAMPLE 4

When erythrocytes are treated with hydrogen peroxide they undergo lipidperoxidation which damages the structure of the cell membrane and the function of the erythrocytes.

In this example the increased damaging effects of the erythrocyte cell membrane when Pb, Hg and Cr were added to the preparations, were investigated. Furthermore, the preventive effect of the presence of D-myo-inositol-1.2.6-triphosphate (IP$_3$) was evaluated.

As described in Example 3 the absorbance at 532 nm was used as a measurement of the amount of lipidperoxides formed and consequently the damage of the erythrocyte cell membrane.

| Experiment | Addition to the reaction mixture (containing erythrocytes, buffer pH 7.4 and H$_2$O$_2$). | Absorbance |
|---|---|---|
| 1 | — | 0.16 |
| 2 | 3 mM IP$_3$ | 0.10 |
| 3 | 0.4 mM Pb$^{2+}$ | 0.22 |
| 4 | 0.4 mM Pb + 3 mM IP$_3$ | 0.13 |
| 5 | 0.4 mM Hg$^{2+}$ | 0.26 |
| 6 | 0.4 mM Hg$^{2+}$ + 3 mM IP$_3$ | 0.15 |
| 7 | 0.4 mM Cr$^{3+}$ | 0.21 |
| 8 | 0.4 mM Cr$^{3+}$ + 3 mM IP$_3$ | 0.14 |

The damage to the cell membranes of the erythrocytes was increased when Pb (Experiment 3), Hg (Experiment 5) or Cr (Experiment 7) was added.

These effects were strongly counteracted by the presence of IP$_3$ (Experiments 4, 6 and 8).

EXAMPLE 5

Hydrolysis of sodium phytate with wheat phytase and fractionation of a mixture of inositolphosphates.

A 1.6 gram quantity of sodium phytate (from corn, Sigma Chemical Co.) was dissolved in 650 ml sodium acetate buffer, pH 5.2. 2.7 gram wheat phytase (EC 3.1.3.26, 0.015 U/mg, from Sigma Chemical Co.) was added and the mixture was incubated at 38° C.

The dephosphorylation was followed by determining the inorganic phosphorus released. After 3 hours when 50% inorganic phosphorus was liberated the hydrolysis was stopped by adding 30 ml ammonia to pH 12. A liquid mixture containing inositolphosphates was obtained. 350 ml of the mixture was passed through an ion-exchange column (Dowex 1, chloride form, 25 mm×250 mm) and eluted with a linear gradient of hydrochloric acid (0–0.7N HCl). Aliquots of eluted fractions were completely hydrolyzed in order to determine the contents of phosphorus and inositol. The peaks correspond to different inositolphosphates, i.e. a peak with the ratio of phosphorus to inositol of three to one consists of inositoltriphosphate etc. Two fractions with the ratio of phosphorus to inositol of three to one were obtained.

EXAMPLE 6

Fractionation of inositoltriphosphates.

100 ml of the first fraction obtained in Example 5 with a phosphorus/inositol ratio of three to one was neutralized and precipitated as a bariumsalt after addition of 10% excess of 0.1M bariumacetate solution. 600 mg of the precipitated salt was dissolved in 50 ml diluted hydrochloric acid. The solution was separated on an ion-exchange column (Dowex 1, chloride form, 25 mm×2500 mm) with diluted hydrochloric acid as eluent. Aliquots of eluted fractions were analyzed for phosphorus. Three peaks consisting of isomers of inositoltriphosphates could be seen.

EXAMPLE 7

Structural determination of isomers of inositoltriphosphates with NMR.

The three peaks obtained in Example 6 were analyzed by H-NMR. Data show that the peaks consist of myo-inositol-1.2.6-triphosphate, myo-inositol-1.2.3-triphosphate and myo-inositol-1.3.4-triphosphate respectively.

The second fraction obtained in Example 5 with a phosphorus/inositol ratio of three to one was analyzed by H-NMR. Data show that the fraction consists of myo-inositol-1.2.5-triphosphate.

EXAMPLE 8

Determination of optical isomers of inositoltriphosphate.

20 mg of the compounds determined with NMR according to Example 7 to be myo-inositol-1.2.6-triphosphate and myo-inositol-1.3.4-triphosphate were further chromatographed on a chiral column based on acetylated cellulose (20 mm×300 mm from Merck) with a mixture of ethanol and water as eluent. The fractions were analyzed with a polarimeter. Each compound consists of one optical isomer, D-myo-inositol-1.2.6-triphosphate and L-myo-inositol-1.3.4-triphosphate respectively.

EXAMPLE 9

Hydrolysis of sodium phytate with baker's yeast and fractionation of a mixture of inositolphosphates.

A 0.7 gram quantity of sodium phytate (from corn, Sigma Chemical Co.) was dissolved in 600 ml sodium acetate buffer pH 4.6. 50 gram of baker's yeast from Jästbolaget, Sweden (dry substance: 28%, nitrogen content: 2%, phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatent was collected.

400 ml of the supernatant was passed through an ion-exchange column (Dowex 1, chloride form, 25 mm×250 mm) and eluted with a linear gradient of hydrochloric acid (0–0.7N HCl).

Aliquots of eluted fractions were completely hydrolyzed in order to determine the contents of phosphorus and inositol. The peaks correspond to different inositolphosphates, i.e. a peak with the ratio of phosphorus to inositol of three to one consists of inositoltriphosphates etc.

EXAMPLE 10

Structural determination of isomers of inositoltriphosphate.

The fraction obtained in Example 9 with a phosphorus/inositol ratio of three to one was neutralized and evaporated before analysis with H-NMR. Data show that the peak consists of myo-inositol-1.2.6-triphosphate.

EXAMPLE 11

Determination of optical isomers of myo-inositol-triphosphate.

The same method was used as described in Example 8 with the difference that 10 mg of the compound determined with NMR according to Example 10 was analyzed. The compound consists of one optical isomer, D-myo-inositol-1.2.6-triphosphate.

EXAMPLE 12

Solution of potassiumsalt of D-myo-inositol-1.2.6-triphosphate for injection.

0.5 g of the potassiumsalt of IP$_3$ and 0.77 g NaCl were dissolved in 98.73 ml of water for injection to form a solution suitable for injection into a person or an animal.

EXAMPLE 13

Tablets of calciumsalt of D-myo-inositol-1.2.6-triphosphate.

Tablets of the calciumsalt of D-myo-inositol-1.2.6-triphosphate were produced in the following way. 50 g calciumsalt of D-myo-inositol-1.2.6-triphosphate, 132 g lactose and 6 g acacia were mixed. Purified water was then added to the mixture, whereupon the mixing was continued until a suitable consistency was obtained. The mixture was sieved and dried. Then the mixture was blended with 10 g talcum and 2 g magnesium stearate. The mixture was compressed into tablets each weighing 200 mg.

EXAMPLE 14

A 0.5 gram quantity of D-chiro-inositol was dissolved in 1 ml phosphoric acid at 60° C. 20 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0N HCl).

The content of the peak with the ratio of phosphorus to inositol of six to one was precipitated by addition of calciumhydroxide. The precipitate was filtered, washed and mixed with 10 ml of a cation-exchange resin to give the acid form of the inositolhexaphosphate. After neutralization with sodium hydroxide and freeze-drying the sodiumsalt of D-chiro-inositolhexaphosphate was obtained.

EXAMPLE 15

A 0.8 gram quantity of the sodium salt of D-chiro-inositolhexaphosphate produced according to Example 14 was dissolved in 300 ml sodium acetate buffer, pH 5.2. 1.3 gram wheat phytase (EC 3.1.3.26 0.015 U/mg from Sigma Chemical Co.) was added and the mixture was incubated at 38° C.

After the liberation of 50% inorganic phosphorus the hydrolysis was stopped by adding ammonia to pH 12.

The mixture containing D-chiro-inositolphosphates was passed through an ion-exchange column (Dowex 1 chloride form, 25 mm×250 mm) and eluted with a linear gradient of hydrochloric acid (0–0.7N HCl).

The peak with the ratio of phosphorus to inositol of three to one was neutralized with 1.0M sodium hydroxide and freeze-dried.

Structural determination with NMR and IR showed the product to be D-chiro-inositoltriphosphate.

EXAMPLE 16

A 0.8 gram quantity of epi-inositol was dissolved in 1.5 ml of phosphoric acid at 60° C. 32 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0N HCl).

The content of the peak with the ratio of phosphorus to inositol of six to one was precipitated by addition of calcium hydroxide. The precipitate was filtered, washed and mixed with 10 ml of a cation-exchange resin to give the acid form of the inositol hexaphosphate. After neutralization with sodium hydroxide and freeze-drying the sodium salt of epi-inositolhexaphosphate was obtained.

EXAMPLE 17

A 1.2 gram quantity of the sodium salt of epi-inositolhexaphosphate produced according to Example 16 was dissolved in 500 ml sodium acetate buffer, pH 5.2. 2.0 gram wheat phytase (EC 3.1.3.26, 0.015 U/mg from Sigma Chemical Co.) was incubated at 38° C.

After the liberation of 50% inorganic phosphorus the hydrolysis was stopped by adding ammonia to pH 12.

The mixture containing epi-inositolphosphates was passed through an ion-exchange column (Dowex 1, chloride form, 25 mm×250 mm) and eluted with a linear gradient of hydrochloric acid (0–0.7N HCl).

The peak with the ratio of phosphorus to inositol of three to one was neutralized with 1.0M sodium hydroxide and freeze-dried.

Structural determination with NMR and IR showed the product to be epi-inositoltriphosphate.

EXAMPLE 18

Forty-five female rats were divided into three groups of fifteen rats each. The three groups of rats were tested to determine their average systolic blood pressure. Each group of fifteen female rats were found to have an average systolic blood pressure of 122 mm Hg.

All forty-five rats of the test were fed a rye-based diet. In the first phase, Phase 1, the first group of fifteen female rats, Group 1, were fed a lead-free diet, whereas the second and third groups of fifteen female rats, Groups 2 and 3, respectively, were additionally provided with drinking water containing 1 part per million (ppm) lead. The Phase 1 feeding continued for three months.

At the end of this period, all forty-five rats were tested to determine their systolic blood pressure. This was accomplished, as in all blood pressure determinations conducted in this test, by the tail cuff method. The Group 1 rats were found to have an unchanged average systolic blood pressure of 122 mm Hg. However, the average systolic blood pressure of the Group 2 and 3 rats were elevated to 133 mm Hg and 132 mm Hg, respectively. This treatment was continued for another 2 months for all three groups without any changes in systolic blood pressure.

In the second phase of this test, Phase 2, the fifteen rats constituting the Group 1 rats continued to be fed a rye-based diet with water free of lead. The fifteen female rats constituting Group 2 were treated with same diet that they were fed in the first phase. That is, the Group 2 rats were fed a rye-based diet with drinking water containing 1 ppm lead. The fifteen rats in Group 3 were also treated in accordance with the feeding schedule of Phase 1. However, they additionally received a daily treatment of 200 ppm D-myo-inositol-1,2,6-triphosphate ($IP_3$) added to the food. This Phase 2 feeding and treatment schedule continued for an additional four weeks.

At the end of that time the systolic blood pressure of each of the forty-five rats constituting Groups 1, 2 and 3 was again tested. The rats of the control group, Group 1, were found to have an average systolic blood pressure of 120 mm Hg. The group 2 rats, which were fed 1 ppm lead-containing water, continued to have an elevated average systolic blood pressure, 134 mm Hg. The fifteen rats, which were also exposed to drinking water containing 1 ppm lead but were also treated with $IP_3$, the Group 3 rats, were found to have recovered their original normal average systolic blood pressure, 121 mm Hg.

EXAMPLE 19

Kidneys were allografted between two incompatible breeds of rabbit (Sandy Lop to New Zealand White).

One pair of rabbits served as a control, while another pair received D-myo-inositol-1.2.6-triphosphate ($IP_3$).

To the donor animals were administered either 0.9% NaCl solution intravenously (control) or $IP_3$ in 0.9% NaCl solution at a dose of 50 mg/kg. After harvesting the kidneys from the donors the organs were flushed at a constant pressure (100 mg Hg) via the renal artery with cold (4° C.) hypertonic citrate, placed in a beaker of 100 ml containing the same solution and stored at 0° C. surrounded by ice in a polystyrene container for a period of 24 hrs.

The recipients were given either 0.9% NaCl solution intravenously (control) or $IP_3$ in 0.9% NaCl solution at a dose of 50 mg/kg for 5 days after the kidney transplantation. The kidney in the control group ceased to pass urine by day 6 and had to be killed by day 9.

The animal receiving $IP_3$ was killed on day 29 but still had good renal function at this time. The results show that $IP_3$ has significant immunosuppressant properties and improved very dramatically the function of allografted kidneys.

EXAMPLE 20

Inflammation of the skin was studied by measuring local oedema formation in the shaved dorsal skin of New Zealand white rabbits in response to intradermal injections of the peptide CGRP and platelet activating factor (PAF). Injections of these compounds intradermally induces an inflammation of the skin and a subsequent oedema formation. The animals were anaesthetized and radioactive ($^{125}I$) human serum albumin (1.5 $\mu$Ci/kg) and Evans Blue (0.5 ml/kg of a 2.5% (w/v) solution were injected intravenously via an ear vein. The spreading of radioactivity and the colour from Evans Blue is used as a measurement of the oedema formation.

Six rabbits were studied in this test and they were given intradermal injections of CGRP and PAF. After receiving albumin and Evans Blue three of the animals were intravenously injected with 50 mg/kg of D-myo-inositol-1.2.6-triphosphate ($IP_3$), while the remaining three were injected with 0.9% NaCl solution.

The oedema formation in the $IP_3$-treated animals was significantly reduced compared to the control group, which shows that $IP_3$ has a marked positive influence on inflammations of the skin.

For purposes of further understanding the invention, formulas are given below of the $IP_3$ isomers of the invention. Formulas are also given for $IP_6$, $IP_5$, $IP_4$ and $IP_2$.

The lower phosphate-esters of myoinositol are named depending on where the phosphoric acid groups are situated on the inositol ring, with the numbering giving as low position numbers as possible. L and D stand for clock-wise and counterclock-wise counting respectively, and are used depending on which result gives the lowest position number. The carbon atom which has an axial phosphoric acid group always has the position number 2. The structural formulas below are simplified to the acid form.

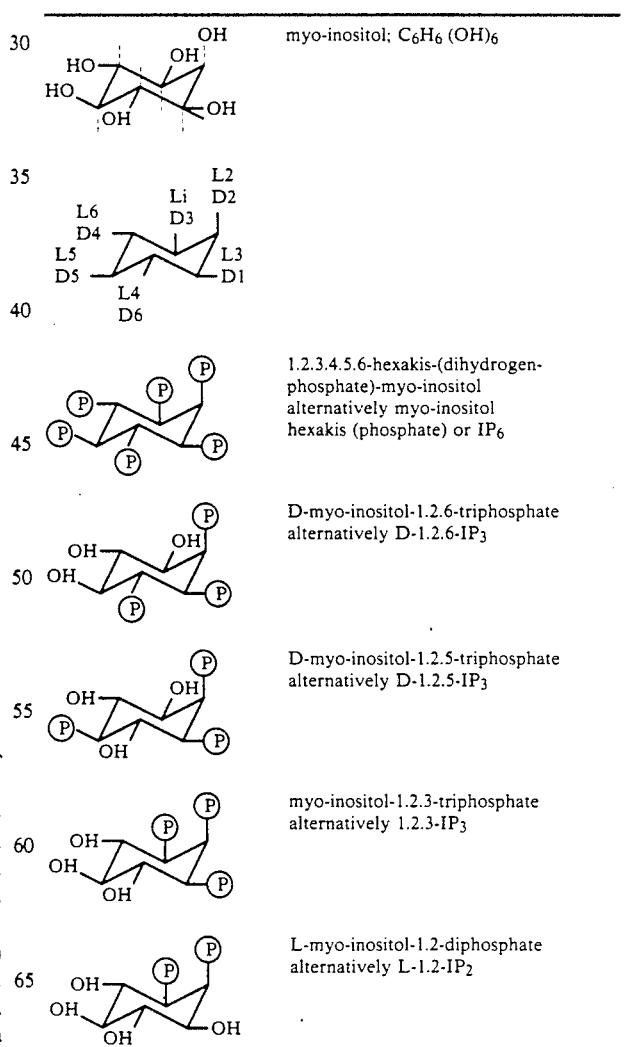

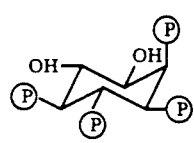

D-myo-inositol-1.2.5.6-tetra-phosphate or D-1.2.5.6-IP₄

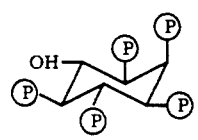

L-myo-inositol-1.2.3.4.5-penta phosphate or L-1.2.3.4.5-IP₅

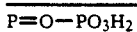

P=O—PO₃H₂

I claim:

1. A method of achieving an immunosuppressant effect in a mammal comprising administering to a mammal in need thereof a pharmaceutical composition which includes an immunosuppressant effective amount of at least one isomer of inositol triphosphate.

2. A method in accordance with claim 1 wherein said isomer of inositol triphosphate is selected from the group consisting of D-myo-inositol-1,2,6-triphosphate, myo-inositol-1,2,3-triphosphate, L-myo-inositol-1,3,4-triphosphate and mixtures thereof.

* * * * *